United States Patent [19]

Tennefos et al.

[11] Patent Number: 5,005,695
[45] Date of Patent: Apr. 9, 1991

[54] CONDOM CADDY PACKAGE

[76] Inventors: David A. Tennefos; Victoria I. Tennefos, both of 2711 S. Rivershore Dr., Moorehead, Minn. 56560

[21] Appl. No.: 493,785

[22] Filed: Mar. 15, 1990

[51] Int. Cl.$^5$ ............................................. B65D 85/00
[52] U.S. Cl. ....................................... 206/69; 206/610; 383/63
[58] Field of Search ................. 206/69, 438, 609, 610, 206/632, 633; 383/61, 63, 65

[56] References Cited

U.S. PATENT DOCUMENTS

| | | | |
|---|---|---|---|
| 4,290,467 | 9/1981 | Schmidt | 383/65 |
| 4,637,061 | 1/1987 | Riese | 383/65 |
| 4,846,585 | 7/1989 | Boeckmann et al. | 383/65 |
| 4,923,309 | 5/1990 | Vanerden | 206/610 |

Primary Examiner—Jimmy G. Foster
Attorney, Agent, or Firm—Leon Gilden

[57] ABSTRACT

A package organization is provided including a front and rear web sealed at their edges to define a package therewithin. The front web includes an elongate tongue cooperative with an elongate groove formed within the rear web. The front and rear webs each include parallel perforated slits mounted in adjacent relationship relative to the upper end of the front and rear webs above the tongue and groove construction to gain access to contents of the package. The tongue and groove construction permits sanitary disposal of a condom contained within the package. Modifications of the invention include a rupturable container secured within the package containing a lubricating germicidal fluid.

6 Claims, 4 Drawing Sheets

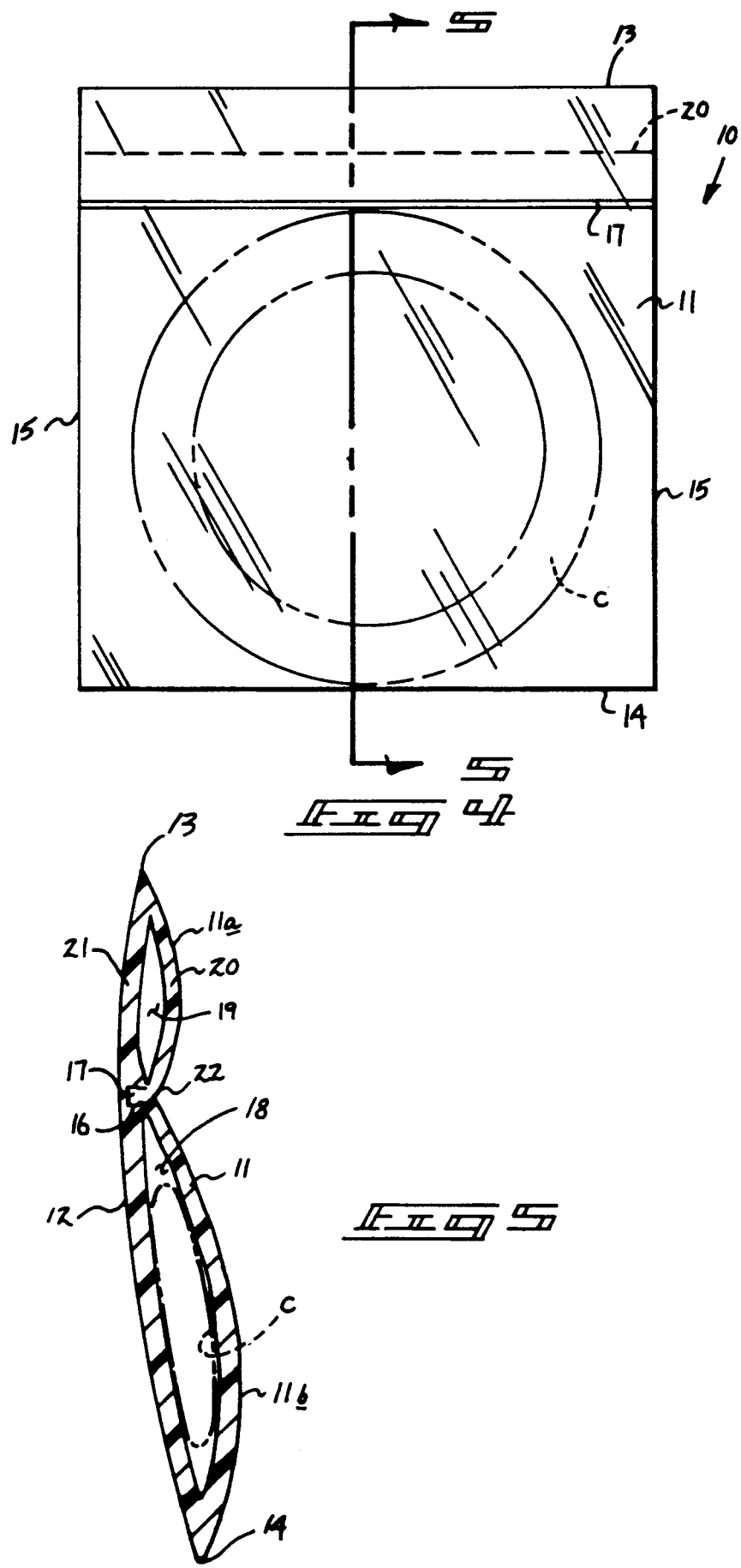

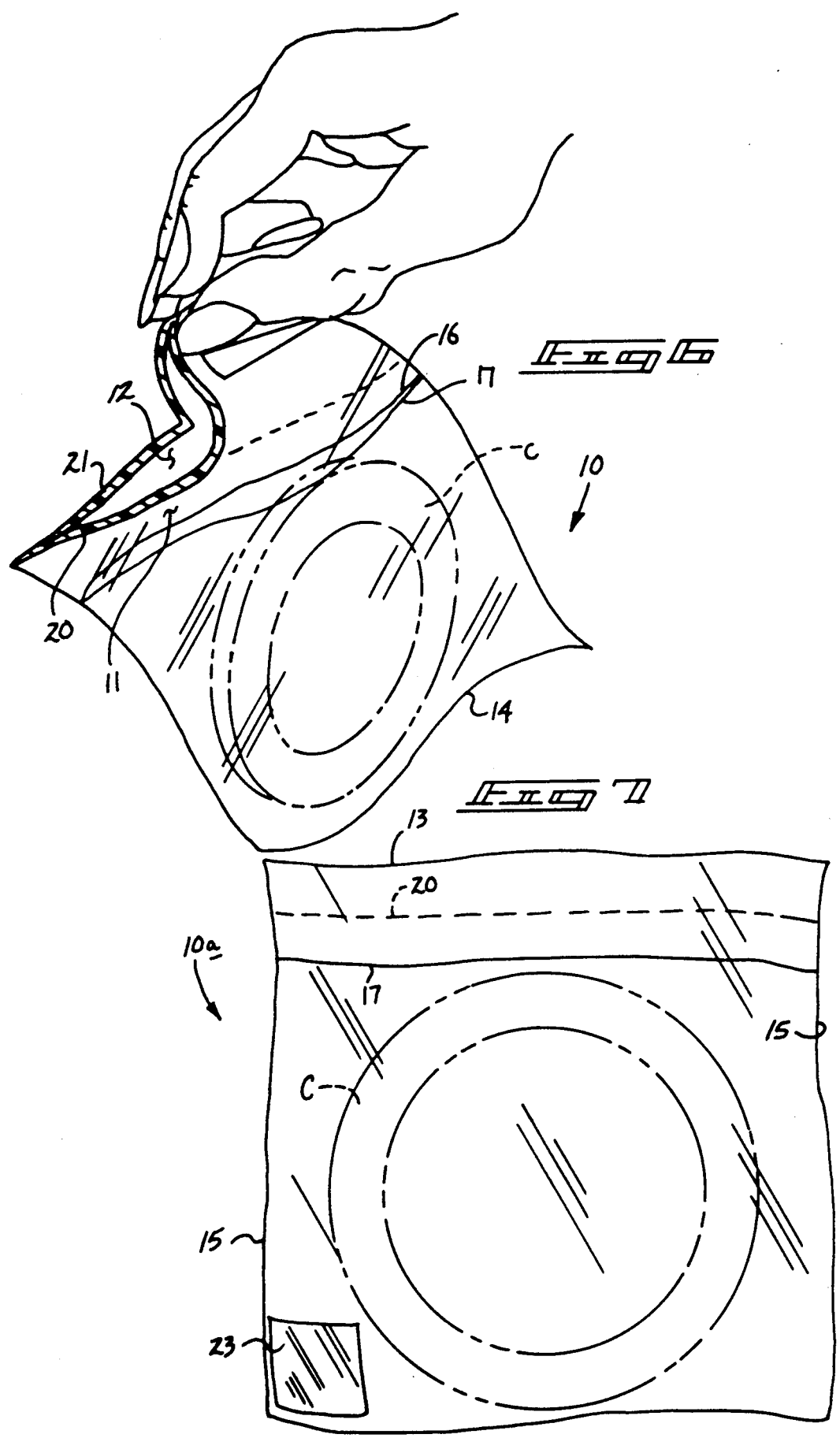

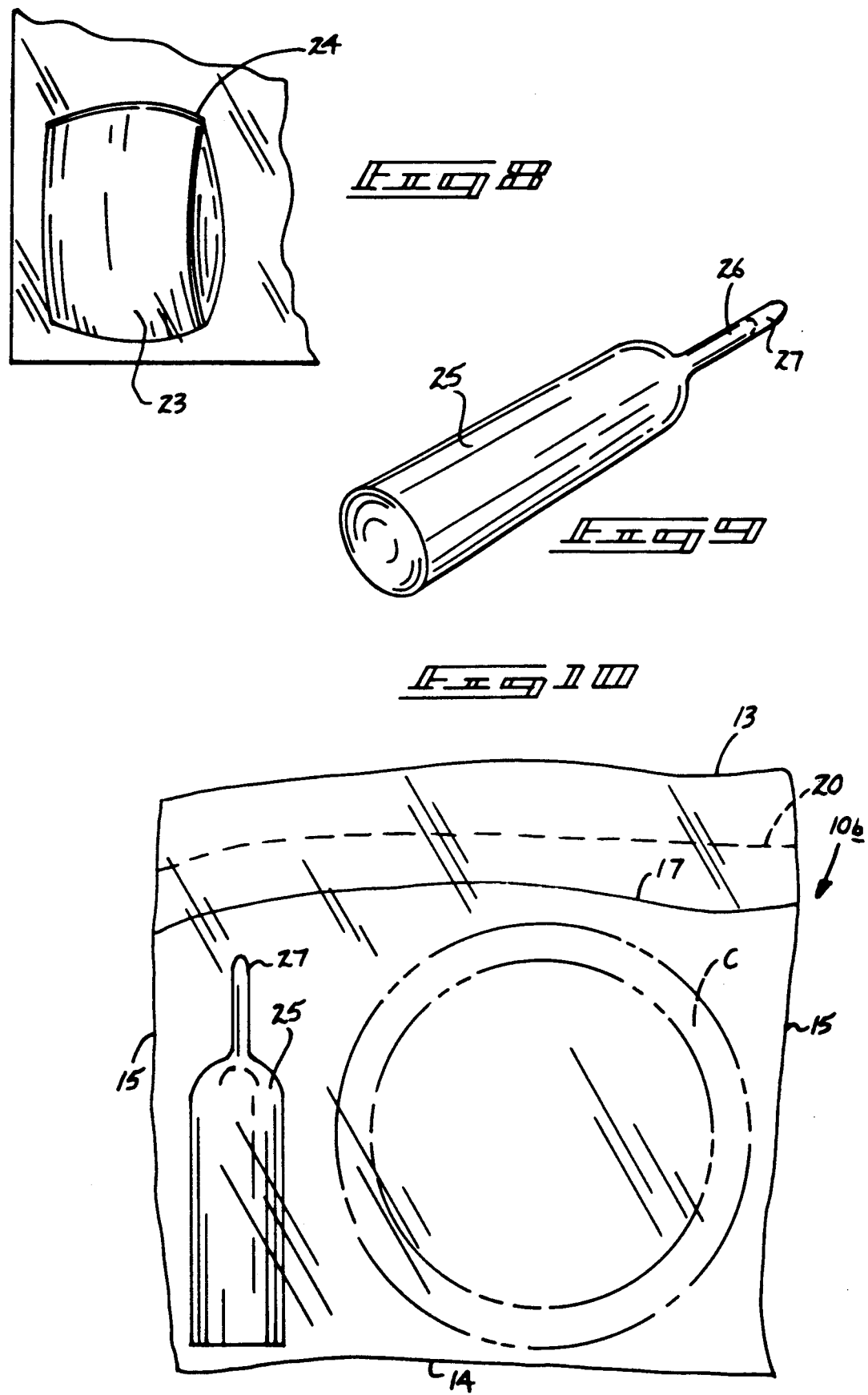

CONDOM CADDY PACKAGE

BACKGROUND OF THE INVENTION

1. Field of the Invention

The field of the invention relates to packages, and more particularly pertains to a condom caddy package wherein the organization permits sanitary disposal of a condom.

2. Description of the Prior Art

Packages containing condoms and the like are notoriously well known in the prior art. Contemporary problems associated with transmitted diseases and the like requires a convenient and readily available manner of disposing of condoms to prevent unnecessary spread of disease and bacteria associated with such items. The instant invention attempts to overcome the deficiencies of the prior art by providing a condom package that provides sanitary and convenient storage of condoms prior to use but further provides for a manner of easy and sanitary disposal of such condoms preventing spread of disease and bacteria associated therewith. Examples of the prior art include U.S. Pat. No. 3,136,417 to CLINCH sets forth a package containing a seamed outer perimeter edge for containment of a condom therewithin in a conventional manner.

U.S. Pat. No. 4,776,460 to HOFFMAN providing an open ended tubular package with concave sides to secure a condom package therewithin.

U.S. Pat. No. 3,282,414 to PENKSA sets forth a hermetically sealed condom package in a annular configuration to secure condom interiorly of an annular rim of the package without providing means of permitting tampering of an associated condom as provided for by the instant invention.

U.S. Pat. No. 2,390,900 to SEHMID sets forth a package construction wherein a generally tubular elongate package slidably receives a condom therewithin with again providing no means of sealing and securing a condom therewithin as does the instant invention.

U.S. Pat. No. 4,738,357 to MARTIN et al sets forth a further means of securing a condom between spaced disks.

As such, there remains a need for a new and improved condom caddy package as set forth by the instant invention which simultaneously prevents tampering and access to a condom contained within a package prior to use and further sets forth a manner of sanitary disposal of the condom and in this respect the present invention substantially fulfills this need.

SUMMARY OF THE INVENTION

In view of the foregoing disadvantages inherent in the known types of condom packages present in the prior art, the present invention provides a new and improved condom caddy package wherein the same provides for sealing and securing a condom within a package prior to use and further provides for secure means to provide for sanitary disposal of the condom. As such, the general purpose of the present invention, which will be described subsequently in greater detail, is to provide a new and improved condom caddy package which has all the advantages of the prior art condom package arrangements and none of the disadvantages.

To attain this, the condom caddy package of the instant invention provides a package organization including a front and rear web sealed at their edges to define a package therewithin. The front web includes an elongate tongue cooperative with an elongate groove formed within the rear web. The front and rear webs each include parallel perforated slits mounted in adjacent relationship relative to the upper end of the front and rear webs above the tongue and groove construction to gain access to contents of the package. The tongue and groove construction permits sanitary disposal of a condom contained within the package. Modifications of the invention include a rupturable container secured within the package containing a lubricating germicidal fluid.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved condom caddy package which has all the advantages of the prior art condom packages and none of the disadvantages.

It is another object of the present invention to provide a new and improved condom caddy package which may be easily and efficiently manufactured and marketed.

It is a further object of the present invention to provide a new and improved condom caddy package which is of a durable and reliable construction.

An even further object of the present invention is to provide a new and improved condom caddy package which is susceptible of a low cost of manufacture with regard to both materials and labor, and which accordingly is then susceptible of low prices of sale to the consuming public, thereby making such condom caddy packages economically available to the buying public.

Still yet another object of the present invention is to provide a new and improved condom caddy package which provides in the apparatuses and methods of the prior art some of the advantages thereof, while simultaneously overcoming some of the disadvantages normally associated therewith.

Still another object of the present invention is to provide a new and improved condom caddy package which may be compactly stored when not being utilized.

Yet another object of the present invention is to provide a new and improved condom caddy package wherein the same provides for secure shielding of a condom within the package prior to use and further permits secure sealing of a condom within the same package for convenient and sanitary disposal thereof.

These together with other objects of the invention, along with the various features of novelty which characterize the invention, are pointed out with particularity in the claims annexed to and forming a part of this disclosure.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 4 is an orthographic side view taken in elevation of the instant invention.

FIG. 5 is an orthographic cross-sectional view taken along the lines 5—5 of FIG. 4 in the direction indicated by the arrows.

FIG. 6 is an isometric illustration of the instant invention illustrating its opening.

FIG. 7 is an orthographic side view taken in elevation of a modified package of the instant invention.

FIG. 8 is an isometric illustration of a rupturable package contained within the package of the instant invention.

FIG. 9 is an isometric illustration of a vial for securement within a further modified package of the instant invention containing the vial.

FIG. 10 is an orthographic side view taken in elevation of the vial contained within the package of the instant invention.

DESCRIPTION OF THE PREFERRED EMBODIMENT

Figure 1:
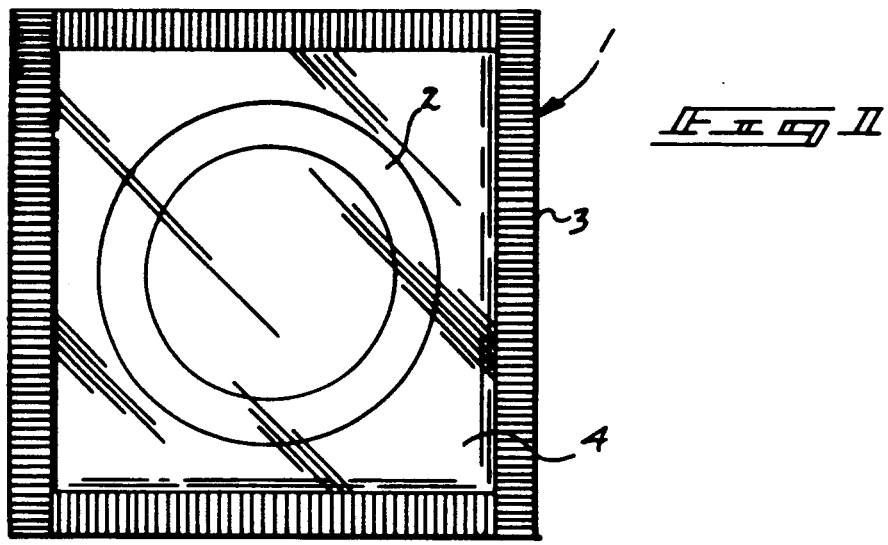
FIG. 1 is an orthographic side view taken in elevation of a prior art condom package.
Figure 2:
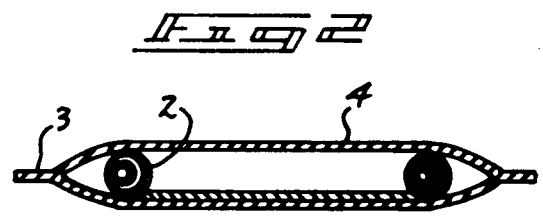
FIG. 2 is an orthographic cross-sectional view of the package as illustrated in FIG. 1.

With reference now to the drawings, and in particular to FIGS. 1 to 10 thereof, a new and improved condom caddy package embodying the principles and concepts of the present invention and generally designated by the reference numerals 10, 10a, and 10b will be described.

Figure 3:
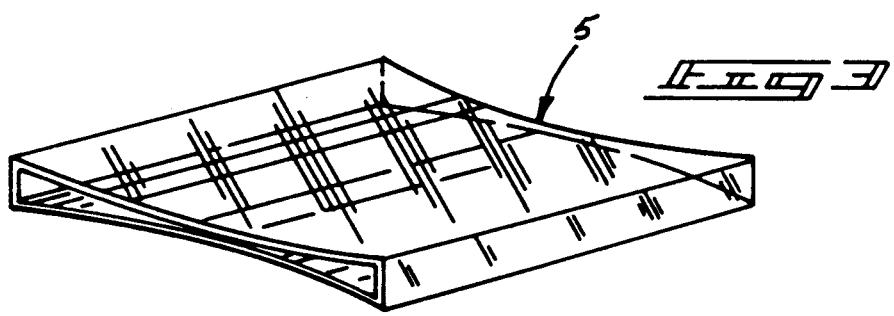
FIG. 3 is a prior art condom package container tube for securement of a condom or package thereof within the tube.

FIG. 1 illustrates a prior art condom package 1 wherein a plurality of spaced webs 4 define a heat sealed perimeter 3 to contain a condom 2 therewithin. FIG. 3 illustrates a tubular container 5 formed with open ends and concave sides to secure a condom or package therewithin for ease of distribution.

FIG. 4 illustrates the condom caddy package 10 of the instant invention wherein a front web 11 is heat seamed to a rear web 12 about its edges defining a heat sealed upper edge 13, a heat sealed lower edge 14, and heat sealed side edges 15. A continuous groove 16 is formed within the rear web 12 arranged generally parallel and adjacent the upper edge 13 to frictionally and sealingly receive a continuous tongue 17 formed within a rear surface of the front web 11. The continuous tongue 17 and groove 16 are coextensive with the front and rear webs 11 and 12 respectively and are mounted in adjacent side by side relationship to permit engagement relative to one another. The tongue 17 is defined by continuous linear recess 22 formed to demarcate an upper convex surface 11a from a lower convex surface 11b of the front web 11. The tongue and groove member 17 and 16 define a upper first compartment 19 from a lower second compartment 18. The second compartment 18 typically contains the condom C therewithin in a sealed relationship and accordingly the second compartment 18 is of a greater volume than the upper or first compartment 19. Formed through the front and rear webs 11 and 12 defined by the second compartment 19 are spaced and aligned parallel front and rear perforated slits 20 and 21 respectively.

The perforated slits permit access to the contents of the package 10 or the condom C. Accordingly it is understood that subsequently, the condom C may be reinserted within the first compartment 18 for subsequent disposal thereof in a sanitary and convenient manner.

FIG. 7 and FIG. 8 illustrate a modified package 10 a wherein a self contained rupturable package 23 is mounted within the first compartment 18. The rupturable package 23 includes a continuous upper lip 24 defining an upper edge of the package 23 that is seamed to a front or rear web surface within the first compartment 18. The rupturable package 23 contains a germicidal lubricant for application to the condom C. FIG. 9 and FIG. 10 illustrate the use of a removable polymeric vial 25 formed with a neck 26 defining a removable tip 27 at a terminal end thereof. A tip is severed from the neck to permit application of a similar germicidal lubricant contained within the vial 25.

As to the manner of usage and operation of the instant invention, the same should be apparent from the above disclosure and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A condom package comprising,
  a front web overlying and coextensive with a rear web, the front web and the rear web including a heat sealed upper edge spaced from a heat sealed lower edge, and heat sealed side edges defining an enclosing perimeter of the package, and a first opening means formed within the front and rear webs adjacent the upper edge for gaining access interiorly of the package, and a second opening means mounted adjacent the first opening means underlying the first opening means for permitting resealing of the package, and a first compartment defined within the package underlying the second opening means, and a second compartment defined within the package overlying the second opening means containing the first opening means, and wherein the first opening means includes a first row of perforated slits formed within the front web extending coextensively along the front web, and further including a second row of perforated slits adjacent to said first row of perforated slits extending coextensively along the rear web wherein the first and second rows of perforated slits are arranged parallel to the top edge spaced above the second opening means, and wherein the second opening means includes a continuous groove extending along the rear web cooperative with a continuous tongue formed to the front web wherein the continuous tongue is defined by a continuous linear recess formed within the front web wherein the linear recess defines a convex upper surface and a convex lower surface extending over the first and second compartments respectively to provide enhanced grasping of the package during opening of the package by rupturing the slits.

2. A package as set forth in claim 1 wherein the first and second opening means extend continuously along the front and rear webs extending to each side of the package.

3. A package as set forth in claim 2 further including a self-contained package contained within the second compartment and a condom contained within the second compartment of the package adjacent the self-contained package.

4. A package as set forth in claim 3 wherein the self-contained package includes a germicidal lubricant therewithin.

5. Apparatus as set forth in claim 4 wherein the self-contained package includes an upper lip wherein the upper lip is seamed to an interior surface within the second compartment prior to use.

6. Apparatus as set forth in claim 4 wherein the self-contained package includes a removable polymeric vial wherein the vial includes a neck and the neck terminates in a forward tip wherein the forward tip is removable to permit dispensing of the germicidal lubricant from within the vial.

* * * * *